(12) United States Patent
Cappiello et al.

(10) Patent No.: US 7,829,587 B2
(45) Date of Patent: Nov. 9, 2010

(54) SUBSTITUTED 2-AMINOTETRALIN DERIVATIVES AS SELECTIVE ALPHA 2B AGONIST

(75) Inventors: John R. Cappiello, Irvine, CA (US); Dario G. Gomez, Rancho Santa Margarita, CA (US); Ken Chow, Newport Coast, CA (US); Michael E. Garst, Newport Beach, CA (US); Daniel W. Gil, Corona Del Mar, CA (US); Larry A. Wheeler, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 514 days.

(21) Appl. No.: 11/971,828

(22) Filed: Jan. 9, 2008

(65) Prior Publication Data

US 2009/0176845 A1 Jul. 9, 2009

(51) Int. Cl.
*C07D 213/04* (2006.01)
*A61K 31/4402* (2006.01)

(52) U.S. Cl. ................... 514/357; 546/333; 546/334
(58) Field of Classification Search ................ None
See application file for complete search history.

(56) References Cited

U.S. PATENT DOCUMENTS 6,953,813 B1 10/2005 Bongrani et al.

FOREIGN PATENT DOCUMENTS

| EP | 0041488 | 12/1981 |
|---|---|---|
| WO | WO 91/00727 | 1/1991 |
| WO | WO 92/00073 | 1/1992 |
| WO | WO 01/08667 | 2/2001 |

OTHER PUBLICATIONS

Kahnt et al, Acta Endocrinologica (1972), 70(2) pp. 315-330.*
Robert R. Ruffolo, Jr., Alpha-Adrenoreceptors: Molecular Biology, Biochemistry and Pharmacology, (Progress in Basic and Clinical Pharmacology series, Karger, 1991).
Holtz et al. , "α-Adrenergic Agents. 3. Behavioral Effects of 2-Aminotetralins" Psychopharmacology 77:259-267 (1982).
DeMarinis et al. , "α-Adrenergic Agents. 1. Direct-Acting $α^1$ Agonists Related to Methoxamine$_1$", J. Med. Chem., 24, 1432-1437, 1981.
DeMarinis et al., "α-Adrenergic Agents. 2. Synthesis and $α_1$-Agonist Activity of 2-Aminotetraline$^{1,2}$" J. Med. Chem. 1982, 25, 136-141.
Ardvidsson et al., "8-Hydroxy-2-(alkylamino)tetralins and Related Compounds as Central 5-Hydroxytryptamine Receptor Agonists", J. Med. Chem., 27, 45-51,1983.

"Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557.
Princen et al., "Evaluation of SDF-1/CXCR4-Induced $Ca^{2+}$ Signaling by Fluorometric Imaging Plate Reader (FLIPR) and Flow Cytometry", Cytometry Part A. 51A, pp. 35-45, 2003.
Arvidsson, Lars-Erik; et al.: 8-Hydroxy-2-(alkylamino)Tetralins and Related Compounds as Central 5-Hydroxytryptamine Receptor Agonists, Journal of Medicinal Chemistry, American Chemical Society, vol. 27, No. 1, Jan. 1, 1984, pp. 45-51.
Cossery, J.M.; et al.: Isosteres Oxygenes D'Hydroxy-DI-N-Propylaminotetralines Synthesis De Monomethoxy Et Monhydroxy-(DI-N-Propylamino)-3 Chromannes UN-Propyl-3H ¾ Racemiques: Nouveaux Radioligands Des Sites De Liasonserotoninergiques 5-HT1A Et Dopaminergiques D2. Ooxigen Isosteres of Hydroxy-DI-N-Propylaminotetrali, Journal of Labelled Compounds and Radiopharmaceuticals, John Wiley, vol. 25, No. 8, Jan. 1, 1988, pp. 833-854.
Holz, W.C.; et al.: α-Adrenergic Agents. 3. Behavioral Effects of 2-Aminotetralins, Psychopharmacology, Springer Verlag, vol. 77, No. 3, Jan. 1, 1982, pp. 259-267.
Horn, Alan S.; et al.: Synthesis and Dopaminergic Activity of a New Oxygen Isostere of the 2-Aminotetralins: N, N-Dipropyl-8-Hydroxy-3-Chromanamine, Eur. J. Med. Chem. vol. 23, 1988, pp. 325-328.
Timmermans, Pieter; et al.: Alpha1alpha2-Adrenoceptor Agonist Selectivity of Mono- and Dihydroxy-2-N, N-DI-n-propylamino-tetralins, European Journal of Pharmacology, vol. 97, No. 1-2, Jan. 13, 1984, pp. 55-65.

* cited by examiner

*Primary Examiner*—Zinna N Davis
(74) *Attorney, Agent, or Firm*—Doina G. Ene; John E. Wurst; Kevin J. Forrestal

(57) ABSTRACT

Substituted 2-aminotetralin derivatives as selective alpha 2B agonists can be incorporated in a pharmaceutical composition and can be used in methods of treating an alpha 2B receptor mediated diseases or conditions. The compounds are represented by Formula 1:

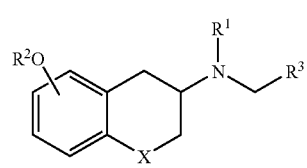

Formula 1 wherein
$R^1$=H, methyl, ethyl, propyl, or cyclobutyl;
$R^2$=methyl or H;
$R^3$=pyridinyl
X=C or O.

19 Claims, No Drawings

SUBSTITUTED 2-AMINOTETRALIN DERIVATIVES AS SELECTIVE ALPHA 2B AGONIST

FIELD OF THE INVENTION

The present disclosure relates to substituted 2-aminotetralin derivatives as selective alpha 2B agonists useful for preparing pharmaceutical compositions.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, beta 1, and beta 2 subtypes. Functional differences between alpha 1 and alpha 2 receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the alpha 1 subtype was reported. The alpha 1/alpha 2 selectivity of this compound was disclosed as being significant because agonist stimulation of the alpha 2 receptors was said to inhibit secretion of epinephrine and norepinephrine, while antagonism of the alpha 2 receptor was said to increase secretion of these hormones. Thus, the use of non-selective alpha-adrenergic blockers, such as phenoxybenzamine and phentolamine, was said to be limited by their alpha 2 adrenergic receptor mediated induction of increased plasma catecholamine concentration and the attendant physiological sequelae (increased heart rate and smooth muscle contraction). For a further general background on the alpha-adrenergic receptors, the reader's attention is directed to Robert R. Ruffolo, Jr., Alpha-Adrenoreceptors: Molecular Biology, Biochemistry and Pharmacology, (Progress in Basic and Clinical Pharmacology series, Karger, 1991), wherein the basis of alpha 1/alpha 2 subclassification, the molecular biology, signal transduction, agonist structure-activity relationships, receptor functions, and therapeutic applications for compounds exhibiting alpha adrenergic receptor affinity is explored.

The cloning, sequencing and expression of alpha receptor subtypes from animal tissues has led to the subclassification of the alpha 1 adrenoreceptors into alpha 1A, alpha 1B, and alpha 1D. Similarly, the alpha 2 adrenoreceptors have also been classified alpha 2A, alpha 2B, and alpha 2C receptors. Each alpha 2 receptor subtype appears to exhibit its own pharmacological and tissue specificities. Compounds having a degree of specificity for one or more of these subtypes may be more specific therapeutic agents for a given indication than an alpha 2 receptor pan-agonist (such as the drug clonidine) or a pan-antagonist.

Among other indications, such as the treatment of glaucoma, hypertension, sexual dysfunction, and depression, certain compounds having alpha 2 adrenergic receptor agonist activity are known analgesics. However, many compounds having such activity do not provide the activity and specificity desirable when treating disorders modulated by alpha 2 adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

Activation of a response at different alpha subtype receptors results in different physiological responses. Thus, compounds which selectively or preferentially activate only one or some of the alpha receptors will be valuable pharmacological tools to probe further the functional role of different alpha 2 receptor subtypes.

U.S. Pat. No. 6,953,813 granted on Oct. 11, 2005 describes 2-aminotetralin derivatives for glaucoma therapy. Holtz et al. in Psychopharmacology (1982) 77:259-267 describe studies with 5-substituted-8-methoxy-2-amino tetralin compounds. DeMarinis et al. in J. Med. Chem. 1981, 24, 1432-1437 describe studies with direct acting alpha 1 agonists related to methoxamine. DeMarinis et al. in J. Med. Chem. 1982, 25, 136-141 describe synthesis and alpha 1 agonist activity of 2-aminotetralins. Ardvidsson et al. in J. Med. Chem. 1983, 27, 45-51 describe 8-hydroxy-2-(alkylamino)tetralins and related compounds as central 5-hydroxytrupamine receptor agonists. WO 91/00727 describes substituted 2-aminotetralins. EP0041488 describes therapeutically useful tetralin derivatives.

SUMMARY OF THE INVENTION

The present disclosure relates to substituted 2-aminotetralin derivatives as selective alpha 2B agonists which include compounds represented by Formula 1:

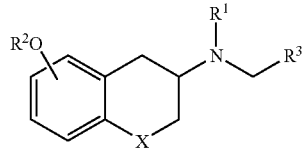

Formula 1 wherein
$R^1$=H, methyl, ethyl, propyl, or cyclobutyl;
$R^2$=methyl or H;
$R^3$=pyridinyl;
X=C or O.

The present disclosure also relates to a pharmaceutical composition containing a pharmaceutical carrier and a therapeutically effective amount of the presently disclosed substituted 2-aminotetralin derivatives which are selective alpha 2B agonists.

The present disclosure also relates to methods of treating an alpha 2B receptor mediated disease or condition by administering a therapeutically effective amount of the presently disclosed substituted 2-aminotetralin derivatives which are selective alpha 2B agonists.

DETAILED DESCRIPTION OF THE INVENTION

The general structures of exemplary specific subtype modulators of alpha 2B and/or alpha 2C adrenergic receptors which are used in the pharmaceutical compositions and methods of treatment are provided by the general Formulas below.

In one aspect of the invention, a compound having selective alpha 2B agonist activity is represented by the general Formula 1:

Formula 1

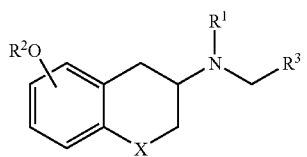

wherein
$R^1$=H, methyl, ethyl, propyl, or cyclobutyl;
$R^2$=methyl or H;
$R^3$=pyridinyl;
X=C or O.

Alternatively, for the compound of Formula 1, $R^1$ can be ethyl or propyl.

Alternatively, for the compound of Formula 1, $R^2$ can be H or methyl.

Pyridinyl is

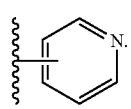

Alternatively, for the compound of Formula 1, $R^3$ is selected from the group consisting of,

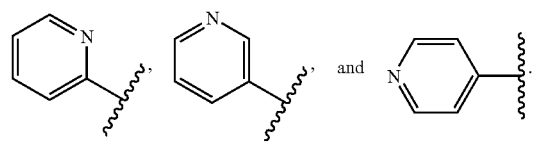

Alternatively, for the compound of Formula 1, X is C.

The following represent exemplary compounds of the present disclosure:

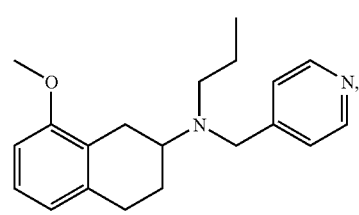

-continued

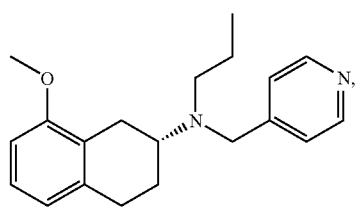

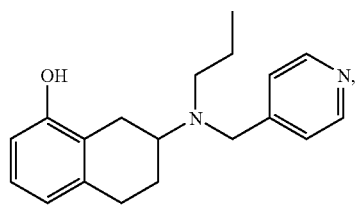

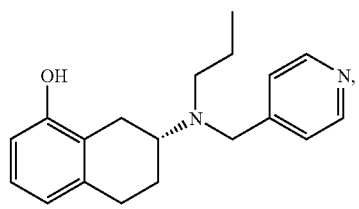

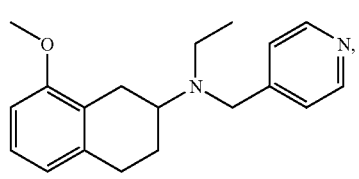

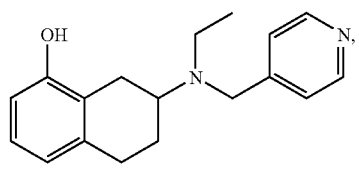

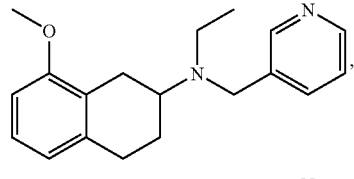

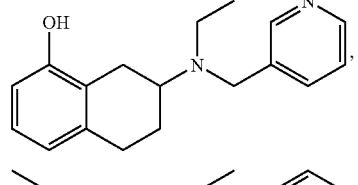

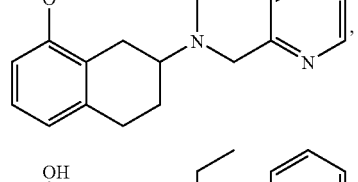

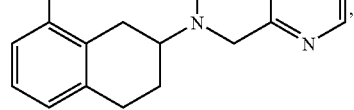

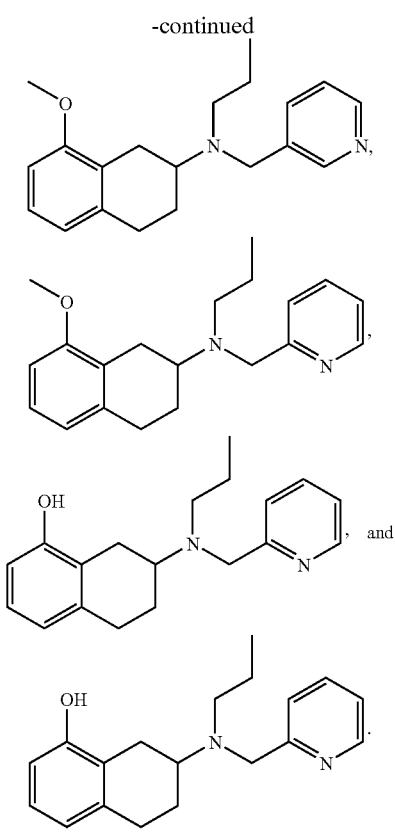

Unless otherwise indicated, reference to a compound should be construed broadly to include pharmaceutically acceptable salts, prodrugs, tautomers, alternate solid forms, non-covalent complexes, and combinations thereof, of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by [tailor this part to the structure being claimed], or some other biologically labile group. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion.

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Exemplary compounds of the invention are disclosed by their structural formulas in the following table together with their potency expressed in nanomolar (nM) as the concentration at which half of their maximal activity is observed ($EC_{50}$). The compound's activity is expressed as its relative efficacy compared to a standard full agonist.

| | $EC_{50}$ nM/(Relative efficacy) FLIPR | | | | |
|---|---|---|---|---|---|
| | α2A | α2B | α2C | α1A | α1B |
| | 1854 (0.22) | 36 (1.0) | 2146 (0.69) | >10K (0) | >10K (0) |
| | 424 (0.34) | potent (1.02) | 557 (0.67) | >10K (0) | >10K (0) |

-continued
| | EC₅₀ nM/(Relative efficacy) FLIPR | | | | |
|---|---|---|---|---|---|
| | α2A | α2B | α2C | α1A | α1B |
| 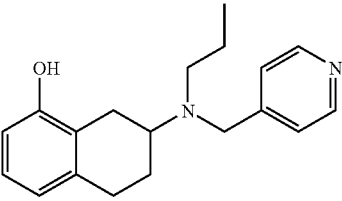 | >10K (0) | 58 (1.06) | ND (0.12) | >10K (0) | >10K (0) |
| 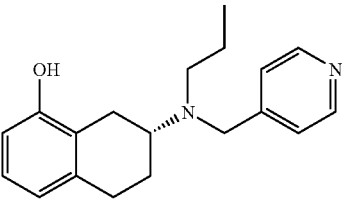 | >10K (0) | 4 (0.8) | >10K (0) | >10K (0) | >10K (0) |
| 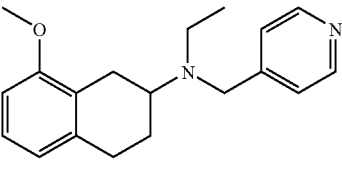 | 203 (0.74) | 78 (0.91) | 253 (0.72) | >10K (0) | >10K (0) |
| 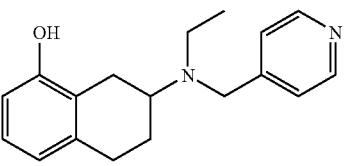 | 5500 (0.16) | 185 (1.08) | 6700 (0.17) | ND (0.1) | ND (0.15) |
| 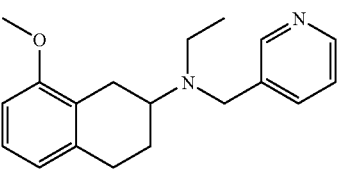 | 442 (0.51) | 614 (0.26) | 652 (0.52) | >10K (0) | >10K (0) |
| 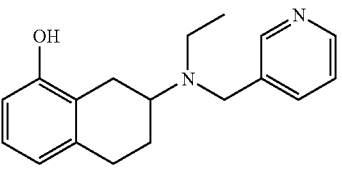 | 4500 (0.35) | 873 (0.89) | ND (0.43) | 4K (0.29) | ND (0.36) |
| 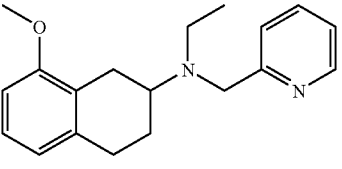 | >10K (0) | 647 (0.14) | >10K (0) | >10K (0) | >10K (0) |
| 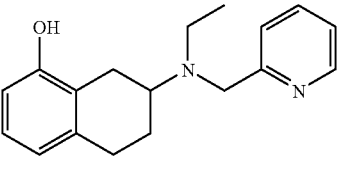 | >10K (0) | 733 (0.28) | >10K (0) | >10K (0) | >10K (0) |

-continued

| | EC$_{50}$ nM/(Relative efficacy) FLIPR | | | | |
|---|---|---|---|---|---|
| | α2A | α2B | α2C | α1A | α1B |
| [8-methoxy-tetrahydronaphthalen-2-yl, N-propyl, N-(pyridin-3-ylmethyl)] | >1000 (0) | 820 (0.47) | ND (0.13) | >10K (0) | >10K (0) |
| [8-methoxy-tetrahydronaphthalen-2-yl, N-propyl, N-(pyridin-2-ylmethyl)] | >10K (0) | 363 (0.63) | >10K (0) | >10K (0) | >10K (0) |
| [8-hydroxy-tetrahydronaphthalen-2-yl, N-propyl, N-(pyridin-2-ylmethyl)] | >10K (0) | 568 (0.69) | >10K (0) | >10K (0) | >10K (0) |
| [8-hydroxy-tetrahydronaphthalen-2-yl, N-propyl, N-(pyridin-2-ylmethyl)] | >10K (0) | 33 (0.95) | >10K (0) | ND (0.05) | >10K (0) |

The compounds disclosed herein are agonists of alpha 2B/2C adrenergic receptors. The alpha2 receptor activity of the compounds of the invention is demonstrated in an assay entitled Fluorometric Imaging Plate Reader (FLIPR) assay (Princen et al., 2003, Cytometry Part A. 51, pp. 35-45). This assay is adequate for monitoring the intracellular Ca$^{2+}$ mobilization from fluorescent reading to evaluate receptor agonists.

FLIPR Ca+2 Influx Assay: HEK 293 cells stably expressing the bovine α1A receptor, the rat α1B receptor, the human α2A receptor and the chimeric G protein G$_{qi5}$, the human α2C receptor and the chimeric G protein G$_{qi5}$ and the mouse α2B receptor and the G$_{α16}$ protein were plated in poly-D-lysine coated 384 well plates at 15,000-25,000 cells per well and grown overnight in DMEM supplemented with 10% fetal bovine serum. For FLIPR (fluorometric image plate reader) evaluation, cells were washed 2-4 times with HBSS/HEPES Buffer (1× Hanks Buffered Salt Solution, 20 mM HEPES<pH 7.4) prior to the addition of Fluo-4-AM (4 uM Fluo-4-AM, 0.04% pluronic acid in HBSS/HEPES Buffer), a calcium-sensitive dye. Cells were loaded with Dye for 40 minutes at 30° C., then washed 4-8 times with HBSS/HEPES Buffer to remove excess dye. Cells were preincubated at 37° C. for 3 minutes prior to placement into the FLIPR instrument. The reaction was carried out at 37° C. and was initiated by the addition of the appropriate dilutions of compounds. The transient calcium was captured and the peak height of the calcium curve determined and utilized for calculation of EC$_{50}$ and efficacy using ActivityBase. Data is stored in the ActivityBase database under the unique identifier "Test Occasion", which reflects the results of an assay run on a particular date and the individual responsible for the assay. Norepinephrine was the standard full agonist for evaluating alpha1 and alpha2 receptor activity.

Diseases and conditions that may be treated in accordance with the compounds disclosed herein, include, but are not limited to the following:

Maculopathies/retinal degeneration diseases and conditions include non-xudative age related macular degeneration (ARMD), exudative age related macular degeneration (ARMD), choroidal neovascularization, diabetic retinopathy, central serous chorioretinopathy, cystoid macular edema, diabetic macular edema and myopic retinal degeneration.

Uveitis/retinitis/choroiditis/other inflammatory diseases and conditions include acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (MEWDS), ocular sarcoidosis, posterior scleritis, serpiginous choroiditis, subretinal fibrosis and uveitis Syndrome, Vogt-Koyanagi-Harada syndrome, punctate inner choroidopathy, acute posterior multifocal placoid pigment epitheliopathy, acute retinal pigment Epitheliitis, and acute macular neuroretinopathy.

Vascular Diseases/exudative diseases include diabetic retinopathy, retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's Disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease.

Traumatic/surgical/environmental diseases and conditions include sympathetic ophthalmia, uveitic retinal disease, retinal detachment, trauma, laser, PDT, photocoagulation, hypoperfusion during surgery, radiation retinopathy and bone marrow transplant retinopathy. Proliferative disorders include proliferative vitreal retinopathy and epiretinal membranes.

Infectious disorders include ocular histoplasmosis, ocular toxocariasis, presumed ocular histoplasmosis syndrome (POHS), endophthalmitis, toxoplasmosis, retinal diseases associated with HIV Infection, choroidal disease associated with HIV Infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis Genetic disorders include retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum Conditions and diseases associated with retinal tears and holes include retinal detachment, macular hole and giant retinal tear.

Conditions and diseases associated tumors include retinal diseases associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors.

Generally speaking alpha 2 agonists can alleviate sympathetically-sensitized conditions that are typically associated with periods of stress. These include the neurological conditions of 1) increased sensitivity to stimuli such as intracranial pressure, light and noise characteristic of migraines and other headaches; 2) the increased sensitivity to colonic stimuli characteristic of Irritable Bowel Syndrome and other GI disorders such as functional dyspepsia; 3) the sensation of itch associated with psoriasis and other dermatological conditions; 4) muscle tightness and spasticity; 5) sensitivity to normally innocuous stimuli such as light touch and spontaneous pain characteristic of conditions like fibromyalgia; 6) various cardiovascular disorders involving hypertension, tachycardia, cardiac ischemia and peripheral vasoconstriction; 7) metabolic disorders including obesity and insulin resistance; 8) behavioral disorders such as drug and alcohol dependence, obsessive-compulsive disorder, Tourette's syndrome, attention deficit disorder, anxiety and depression; 9) altered function of the immune system such as autoimmune diseases including lupus erythematosis and dry eye disorders; 10) chronic inflammatory disorders such as Crohn's disease and gastritis; 11) sweating (hyperhydrosis) and shivering; and 12) sexual dysfunction.

Alpha 2 agonists including alpha 2B/2C agonists are also useful in the treatment of glaucoma, elevated intraocular pressure, neurodegenerative diseases including Alzheimer's, Parkinsons, ALS, schizophrenia, ischemic nerve injury such as stroke or spinal injury, and retinal injury as occurs in glaucoma, macular degeneration, diabetic retinopathy, retinal dystrophies, Lebers optic neuropathy, other optic neuropathies, optic neuritis often associated with multiple sclerosis, retinal vein occlusions, and following procedures such as photodynamic therapy and LASIX. Also included are chronic pain conditions such as cancer pain, post-operative pain, allodynic pain, neuropathic pain, CRPS or causalgia, visceral pain.

The compounds are used in accordance with the present disclosure as highly effective analgesics, particularly in chronic pain models, with minimal undesirable side effects, such as sedation and cardiovascular depression, commonly seen with other agonists of the alpha 2 receptors.

In accordance with the invention, the present compounds may be administered at pharmaceutically effective dosages. Such dosages are normally the minimum dose necessary to achieve the desired therapeutic effect; in the treatment of chronic pain, this amount would be roughly that necessary to reduce the discomfort caused by the pain to tolerable levels. The actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any pharmacologically acceptable form, such as a tablet, liquid, capsule, powder and the like. However, other routes may be desirable or necessary, particularly if the patient suffers from nausea. Such other routes may include transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

Another aspect of the present disclosure is drawn to therapeutic compositions comprising the presently disclosed compounds and a pharmaceutically acceptable carrier. The carrier may be solid, semi-solid, or liquid material that acts as an excipient or vehicle for the active compound. The formulations may also include wetting agents, emulsifying agents, preserving agents, sweetening agents, and/or flavoring agents. If used in an ophthalmic or infusion format, the formulation will usually contain one or more salts to adjust the osmotic pressure of the formulation.

Another aspect of the present disclosure is drawn to methods for treatment of alpha 2B receptor mediated disease or condition through administration of one or more of the presently disclosed compounds.

The alpha 2B receptor mediated disease or condition may include but is not limited to glaucoma, elevated intraocular pressure, ischemic neuropathies, optic neuropathy, pain, visceral pain, corneal pain, headache pain, migraine, cancer pain, back pain, irritable bowl syndrome pain, muscle pain and pain associated with diabetic neuropathy, the treatment of diabetic retinopathy, other retinal degenerative conditions, stroke, cognitive deficits, neropsychiatric conditions, drug dependence and addiction, withdrawal of symptoms, obsessive-compulsive disorders, obesity, insulin resistance, stress-related conditions, diarrhea, diuresis, nasal congestion, spasticity, attention deficit disorder, psychoses, anxiety, depression, autoimmune disease, Crohn's disease, gastritis, Alzheimer's, and Parkinson's ALS.

It is known that chronic pain (such as pain from cancer, arthritis, and many neuropathic injuries) and acute pain (such as that pain produced by an immediate mechanical stimulus, such as tissue section, pinch, prick, or crush) are distinct neurological phenomena mediated to a large degree either by different nerve fibers and neuroreceptors or by a rearrangement or alteration of the function of these nerves upon chronic stimulation. Sensation of acute pain is transmitted quite quickly, primarily by afferent nerve fibers termed C fibers, which normally have a high threshold for mechanical, thermal, and chemical stimulation. While the mechanisms of chronic pain are not completely understood, acute tissue injury can give rise within minutes or hours after the initial stimulation to secondary symptoms, including a regional reduction in the magnitude of the stimulus necessary to elicit a pain response. This phenomenon, which typically occurs in a region emanating from (but larger than) the site of the original stimulus, is termed hyperalgesia. The secondary response can give rise to profoundly enhanced sensitivity to mechanical or thermal stimulus.

The A afferent fibers can be stimulated at a lower threshold than C fibers, and appear to be involved in the sensation of chronic pain. For example, under normal conditions, low threshold stimulation of these fibers (such as a light brush or tickling) is not painful. However, under certain conditions such as those following nerve injury or in the herpes virus-mediated condition known as shingles the application of even such a light touch or the brush of clothing can be very painful. This condition is termed allodynia and appears to be mediated at least in part by A afferent nerves. C fibers may also be involved in the sensation of chronic pain, but if so it appears clear that persistent firing of the neurons over time brings about some sort of change which now results in the sensation of chronic pain.

By "acute pain" is meant immediate, usually high threshold, pain brought about by injury such as a cut, crush, burn, or by chemical stimulation such as that experienced upon exposure to capsaicin, the active ingredient in chili peppers.

By "chronic pain" is meant pain other than acute pain, such as, without limitation, neuropathic pain, visceral pain (including that brought about by Crohn's disease and irritable bowel syndrome (IBS)), and referred pain.

EXAMPLES

Example A

Procedure for the Preparation of Benzyl-(8-methoxy-1,2,3,4-tetrahydro-naphthalen-2-yl)-propyl-amine

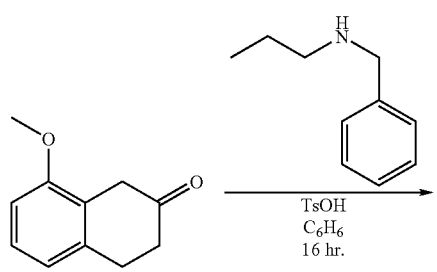

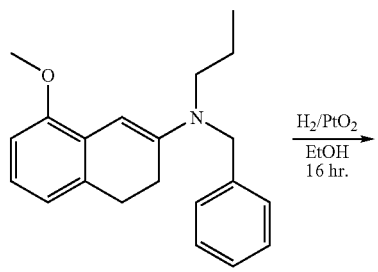

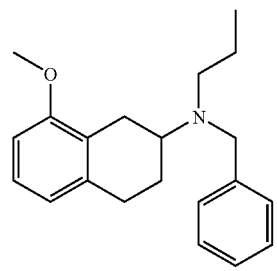

8-Methoxy-2-tetralone (1) (1.1 g, 6.7 mmol, 1.0 equiv) and propyl benzyl amine (1.0 g, 6.7 mmol, 1.0 equiv) in benzene (100 mL) was treated with p-toluenesulfonic acid (0.13 g, 0.67 mmol, 0. lequiv). The reaction vessel was fitted with a Dean-Stark trap and the solution heated to reflux for 16 hr. The solution was cooled to rt and quenched with a 20% KOH solution and the product extracted with EtOAc. The organic layers were combined and dried over $M_gSO_4$. The organic layer was fitered and evaporated under vacuum. The crude olefin (2) was used directly in the next step.

A solution of (2) in 100 mL of ethanol was hydrogenated over 0.15 g (0.67 mmol, 0.1 equiv) of platinum oxide at balloon pressure. After the reaction mixture was stirred overnight Celite was added to the solution and the catalyst removed by filtration. The filtrate was evaporated to give the crude tetralin (3). Column chromatography (50:1 dichloromethane/methanol sat'd with ammonia) afforded 0.98 g (47%) of (3) as a reddish sap. $^1$H NMR (300 MHz, <DMSO>) δ ppm 0.81 (t, J=7.33 Hz, 3 H) 1.39 (sxt, J=7.21 Hz, 2 H) 1.47-1.63 (m, 1 H) 1.96 (d, J=12.02 Hz, 1 H) 2.36-2.48 (m, 2 H) 2.61-2.75 (m,1 H) 2.75-2.89 (m, 3 H) 3.17 (d, J=5.28 Hz, 1 H) 3.59-3.74 (m, 2 H) 3.75 (s, 3 H) 6.64 (d, J=7.62 Hz, 1 H) 6.71 (d, J=7.92 Hz, 1 H) 7.03 (t, J=7.77 Hz, 1 H) 7.15-723 (m, 1 H) 729 (t, J=7.33 Hz, 2 H) 7.33-7.38 (m, 2 H).

Example A-1

(8-Methoxy-1,2,3,4-tetrahydro-naphthalen-2-yl)-propyl-pyridin-2-ylmethyl-amine is prepared by substituting propyl-pyridin-2-ylmethyl-amine in the method of A. $^1$H NMR (500 MHz, <CDCl$_3$>) δ ppm 0.88 (t, J=7.32 Hz, 3 H) 1.43-1.51 (m, J=7.57, 7.38, 7.38, 7.38, 7.38 Hz, 2 H) 1.60-1.66 (m, 1 H) 2.05-2.11 (m, 1 H) 2.48-2.56 (m, 1 H) 2.56-2.65 (m, 2 H) 2.75-2.84 (m, 1 H) 2.86-2.92 (m, 1 H) 2.93-3.04 (m, 2 H) 3.83 (s, 3 H) 3.84-3.96 (m, 2 H) 6.65 (d, J=8.30 Hz, 1 H) 6.70 (d, J=7.32 Hz, 1 H) 7.08 (t, J=8.06 Hz, 1 H) 7.11-7.14 (m, 1 H) 7.64-7.67 (m, 2 H) 8.49 (d, J=4.88 Hz, 1 H).

Example A-2

(8-Methoxy-1,2,3,4-tetrahydro-naphthalen-2-yl)-propyl-pyridin-4-ylmethyl-amine is prepared by substituting propyl-pyridin-4-ylmethyl-amine in the method of A. $^1$H NMR (300 MHz, <CDCl$_3$>) δ ppm 0.88 (t, J=7.33 Hz, 3 H) 1.46 (sxt, J=7.33 Hz, 2 H) 1.55-1.70 (m, J=11.98, 6.30, 5.95, 5.95 Hz, 1 H) 1.97-2.08 (m, J=9.75, 4.84, 2.38, 2.38 Hz, 1 H) 2.42-2.51 (m, 1 H) 2.51-2.63 (m, 2 H) 2.73-3.14 (m, 4 H) 3.73 (d, J=4.69 Hz, 2 H) 3.83 (s, 3 H) 6.66 (d, J=7.92 Hz, 1 H) 6.70 (d, J=7.62 Hz, 1 H) 7.08 (t, J=7.77 Hz, 1 H) 7.34-7.38 (m, 2 H) 8.49-8.52 (m, 2 H).

Example A-4

Ethyl-(8-methoxy-1,2,3,4-tetrahydro-naphthalen-2-yl)-pyridin-4-ylmethyl-amine is prepared by substituting ethyl-pyridin-4-ylmethyl-amine in the method of A. $^1$H NMR (300 MHz, <CDCl3>) δ ppm 1.05 (t, J=7.04 Hz, 3 H) 1.60-1.71 (m, 1 H) 2.03 (dt, J=15.46, 2.38 Hz, 1 H) 2.50 (dd, J=17.88, 12.02 Hz, 1 H) 2.66 (dd, J=7.18, 4.84 Hz, 2 H) 2.77-2.90 (m, 2 H) 2.91-3.04 (m, 2 H) 3.73 (d, J=1.47 Hz, 2 H) 3.83 (s, 3 H) 6.66 (d, J=7.92 Hz, 1 H) 6.70 (d, J=7.62 Hz, 1 H) 7.09 (t, J=7.92 Hz, 1 H) 7.36 (d, J=6.16 Hz, 2 H) 8.49-8.53 (m, 2 H).

Example A-3

Ethyl-(8-methoxy-1,2,3,4-tetrahydro-naphthalen-2-yl)-pyridin-3-ylmethyl-amine is prepared by substituting ethyl-pyridin-3-ylmethyl-amine in the method of A. $^1$H NMR (300 MHz, <CDCl$_3$>) δ ppm 1.05 (t, J=7.04 Hz, 3 H) 1.57-1.73 (m, J=11.95, 11.84, 11.84, 5.72 Hz, 2 H) 2.03 (dddd, J=12.20, 4.95, 2.78, 2.64 Hz, 1 H) 2.44-2.60 (m, 1 H) 2.62 (qd, 3 H) 2.78-2.90 (m, 1 H) 2.91-3.04 (m, 2 H) 3.74 (d, J=2.64 Hz, 2 H) 3.83 (s, 3 H) 6.66 (d, J=8.21 Hz, 1 H) 6.70 (d, J=7.92 Hz, 1 H) 7.08 (t, J=7.77 Hz, 1H) 7.21-7.27 (m, 0 H) 7.76 (dt, J=7.62, 1.91 Hz, 1 H) 8.46 (dd, J=4.69, 1.76 Hz, 1 H) 8.60 (d, J=1.47 Hz, 1 H).

Example A-5

Ethyl-(8-methoxy-1,2,3,4-tetrahydro-naphthalen-2-yl)-pyridin-2-ylmethyl-amine is prepared by substituting ethyl-pyridin-2-ylmethyl-amine in the method of A. $^1$H NMR (300 MHz, <CDCl$_3$>) δ ppm 1.07 (t, J=7.04 Hz, 3 H) 1.64 (qd, J=11.82, 5.57 Hz, 1 H) 2.03-2.13 (m, 1 H) 2.53 (dd, J=18.32, 12.46 Hz, 1 H) 2.64-2.79 (m, 2 H) 2.80-2.95 (m, 2 H) 2.95-3.07 (m, 2 H) 3.82 (s, 3 H) 3.89 (s, 2 H) 6.65 (d, J=7.92 Hz, 1 H) 6.70 (d, J=7.62 Hz, 1 H) 7.04-7.09 (m, 1 H) 7.10-7.15 (m, 1 H) 7.62-7.68 (m, 2 H) 8.50 (d, J=4.69 Hz, 1 H).

Example A-6

(8-Methoxy-1,2,3,4-tetrahydro-naphthalen-2-yl)-propyl-pyridin-3-ylmethyl-amine is prepared by substituting propyl-pyridin-3-ylmethyl-amine in the method of A. $^1$H NMR (300 MHz, <CDCl$_3$>) δ ppm 0.86 (t, J=7.33 Hz, 3 H) 1.46 (sxt, J=7.33 Hz, 2 H) 1.64 (qd, J=11.92, 5.28 Hz, 1 H) 1.98-2.07 (m, J=9.71, 4.87, 2.24, 2.24 Hz, 1 H) 2.44 Hz, 1 H) 2.44-2.62 (m, J=7.11, 7.11, 3.52, 3.37 Hz, 4 H) 2.72-3.03 (m, 4 H) 3.73 (d, J=5.86 Hz, 2 H) 3.83 (s, 3 H) 6.66 (d, J=8.21 Hz, 1 H) 6.70 (d, J=7.62 Hz, 1 H) 7.24 (d, J=4.69 Hz, 1 H) 7.72-7.78 (m, 1 H) 8.46 (dd, J=4.84, 1.32 Hz, 1 H) 8.60 (d, J=2.35 Hz, 1 H).

Example B

Procedure for the Preparation of 7-[benzyl(propyl)amino]-5,6,7,8-tetrahydronaphthalen-1-ol

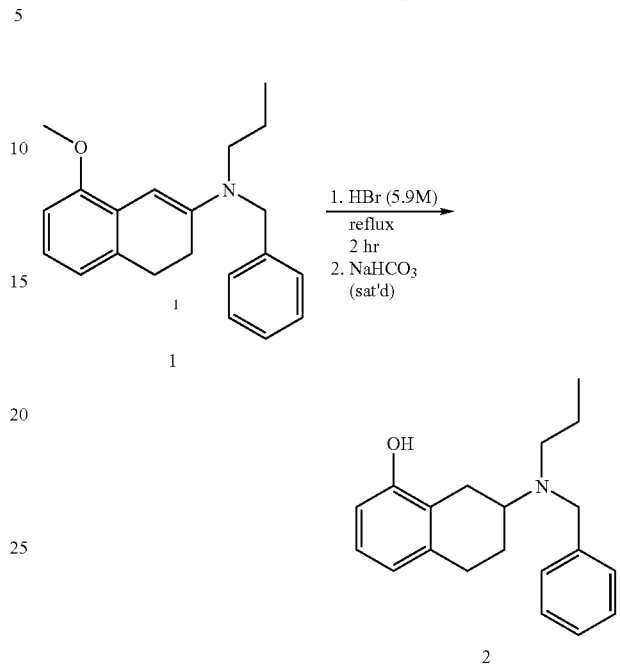

Benzyl-(8-methoxy-1,2,3,4-tetrahydro-naphthalen-2-yl)-propyl-amine (1) (0.68 g, 2.2 mmol, 1.0 equiv) was treated with HBr (5.0 mL of a 5.9M solution, 29 mmol, 13 equiv) and heated to reflux for 2 hours. The solution was cooled and quenched with 100 mL of a saturated solution of NaHCO$_3$ and the product extracted with EtOAc. The organic layers were combined and dried over MgSO$_4$. The organic layer was filtered and evaporated under vacuum. The concentrated product (2) (0.51 g, 79%) was isolated as a dark colored sap and pure by NMR and MS analysis. $^1$H NMR (300 MHz, <DMSO>) δ ppm 0.81 (t, J=7.33 Hz, 3 H) 1.32-1.46 (m, J=7.33, 7.18, 7.18, 7.18, 7.18 Hz, 2 H) 1.47-1.62 (m, 1 H) 1.87-2.00 (m, 1 H) 2.33-2.49 (m, 2 H) 2.56-2.72 (m, 2 H) 2.71-2.89 (m, 3 H) 3.57-3.77 (m, 2 H) 6.48 (d, J=7.62 Hz, 1 H) 6.57 (d, J=7.62 Hz, 1 H) 6.85 (t, J=7.62 Hz, 1 H) 7.14-7.24 (m, 1 H) 7.29 (t, J=7.33 Hz, 2 H) 7.33-7.40 (m, 2 H) 9.18 (s, 1 H).

Example B-1

7-(Propyl-pyridin-4-ylmethyl-amino)-5,6,7,8-tetrahydro-naphthalen-1-ol is prepared by substituting (8-Methoxy-1,2,3,4-tetrahydro-naphthalen-2-yl)-propyl-pyridin-4-ylmethyl-amine in the method of B. $^1$H NMR (300 MHz, <DMSO>) δ ppm 0.82 (t, J=7.33 Hz, 3 H) 1.32-1.46 (m, J=7.33, 7.18, 7.18, 7.18, 7.18 Hz, 2 H) 1.47-1.63 (m, 1 H) 1.89-1.98 (m, 1 H) 2.32-2.54 (m, 3 H) 2.60-2.88 (m, 4 H) 3.63-3.80 (m, 2 H) 6.49 (d, J=7.62 Hz, 1 H) 6.57 (d, J=7.33 Hz, 1 H) 6.86 (t, J=7.77 Hz, 1 H) 7.39 (dd, J=4.25, 1.61 Hz, 2 H) 8.48 (dd, J=4.40, 1.47 Hz, 2 H) 9.20 (s, 1 H).

Example B-2

7-(Propyl-pyridin-2-ylmethyl-amino)-5,6,7,8-tetrahydro-naphthalen-1-ol is prepared by substituting (8-Methoxy-1,2,3,4-tetrahydro-naphthalen-2-yl)-propyl-pyridin-2-yimethyl-amine in the method of B. $^1$H NMR (300 MHz, <CDCl33>)

δ ppm 0.89 (t, J=7.33 Hz, 3 H) 1.40-1.72 (m, 5 H) 2.09 (br. s., 1 H) 2.52-2.70 (m, 3 H) 2.72-2.89 (m, 2 H) 2.90-3.08 (m, 2 H) 3.93 (br. s., 2 H) 6.62 (d, J=8.21 Hz, 1 H) 6.66 (d, J=7.04 Hz, 1 H) 6.98 (t, J=7.92 Hz, 1 H) 7.13-7.21 (m, 1 H) 7.62-7.73 (m, 2 H) 8.52 (d, J=5.57 Hz, 1 H).

Example B-3

7-(Ethyl-pyridin-3-yimethyl-amino)-5,6,7,8-tetrahydro-naphthalen-1-ol is prepared by substituting ethyl-(8-methoxy-1,2,3,4-tetrahydro-naphthalen-2-yl)-pyridin-3-yimethyl-amine in the method of B. $^1$H NMR (300 MHz, <DMSO>) δ ppm 0.98 (t, J=6.60 Hz, 3 H) 1.47-1.64 (m, 1 H) 1.89-1.99 (m, 1 H) 2.31-2.47 (m, 1 H) 2.52-2.96 (m, 6 H) 3.70 (d, J=5.28 Hz, 2 H) 6.50 (d, J=7.33 Hz, 1 H) 6.57 (d, J=7.33 Hz, 1 H) 6.86 (t, J=7.77 Hz, 1 H) 7.34 (d, J=7.33 Hz, 1 H) 7.76 (d, J=8.50 Hz, 1 H) 8.42 (d, J=4.40 Hz, 1 H) 8.55 (s, 1 H) 9.18 (s, 1 H).

Example B-4

7-(Ethyl-pyridin-4-yimethyl-amino)-5,6,7,8-tetrahydro-naphthalen-1-ol is prepared by substituting ethyl-(8-methoxy-1,2,3,4-tetrahydro-naphthalen-2-yl)-pyridin-4-ylmethyl-amine in the method of B. $^1$H NMR (300 MHz, <CDCl3>) δ ppm 1.06 (t, J=7.18 Hz, 3 H) 1.65 (qd, J=11.78, 5.42 Hz, 1 H) 1.99-2.10 (m, 1 H) 2.50-2.73 (m, 3 H) 2.73-2.91 (m, 2 H) 2.92-3.10 (m, 3 H) 3.75 (d, J=2.93 Hz, 2 H) 6.58-6.71 (m, 2 H) 6.98 (t, J=7.77 Hz, 1 H) 7.40 (d, J=5.57 Hz, 2 H) 8.52 (d, J=5.86 Hz, 2 H).

Example B-5

7-(Ethyl-pyridin-2 ylmethyl-amino)-5,6,7,8-tetrahydro-naphthalen-1-ol is prepared by substituting ethyl-(8-methoxy-1,2,3,4-tetrahydro-naphthalen-2-yl)-pyridin-2-ylmethyl-amine in the method of B. $^1$H NMR (300 MHz, <DMSO>) δ ppm 0.99 (t, J=6.52 Hz, 3 H) 1.55 (d, J=6.30 Hz, 1 H) 1.95 (d, J=8.65 Hz, 1 H) 2.43 (d, J=12.02 Hz, 1 H) 2.55-3.00 (m, 6 H) 3.79 (br. s., 2 H) 6.49 (d, J=7.48 Hz, 1 H) 6.57 (d, J=7.77 Hz, 1 H) 6.86 (t, J=7.70 Hz, 1 H) 7.21 (br. s., 1 H) 7.56 (d, J=7.92 Hz, 1 H) 7.75 (t, J=7.04 Hz, 1 H) 8.45 (br. s., 1 H) 9.19 (br. s., 1 H).

Example B-6

7-(Propyl-pyridin-3-ylmethyl-amino)-5,6,7,8-tetrahydro-naphthalen-1-ol is prepared by substituting (8-Methoxy-1,2,3,4-tetrahydro-naphthalen-2-yl)-propyl-pyridin-3-ylmethyl-amine in the method of B. $^1$H NMR (300 MHz, <DMSO>) δ ppm 1.30-1.44 (m, 2 H) 1.49-1.63 (m, 1 H) 1.88-2.02 (m, 1 H) 2.32-2.47 (m, 1 H) 2.62-2.94 (m, 4 H) 2.65-2.90 (m, 3 H) 3.17 (d, J=5.28 Hz, 2 H) 3.56-3.84 (m, 2 H) 6.49 (d, J=7.33 Hz, 1 H) 6.57 (d, J=7.92 Hz, 1 H) 6.86 (t, J=7.92 Hz, 1 H) 7.33 (dd, J=7.18, 5.13 Hz, 1 H) 7.75 (d, J=7.92 Hz, 1 H) 8.42 (d, J=3.81 Hz, 1 H) 8.54 (s, 1 H) 9.18 (s, 1 H).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:
1. A compound having Formula 1

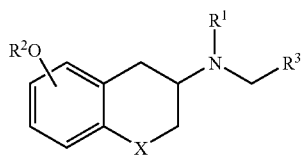

Formula 1 wherein:
$R^1$=H, methyl, ethyl, propyl, or cyclobutyl;
$R^2$=methyl or H;
$R^3$=pyridinyl;
X=C.

2. The compound of claim 1 wherein $R^1$ is ethyl or propyl.
3. The compound of claim 1, wherein $R^2$ is H or methyl.
4. The compound of claim 1, wherein $R^3$ is selected from the group consisting of

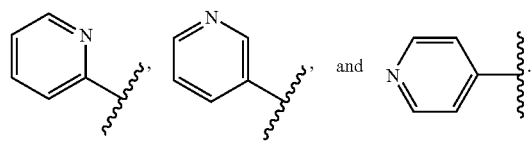

5. The compound of claim 1, wherein X is C.
6. The compound of claim 1 selected from the group consisting of:

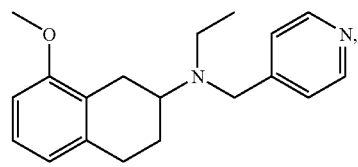

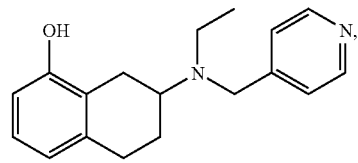

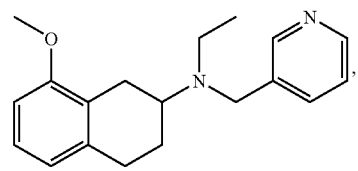

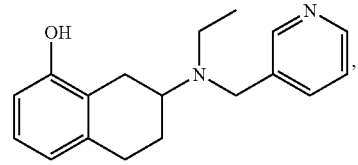

-continued

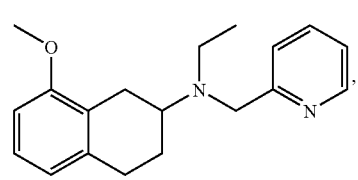

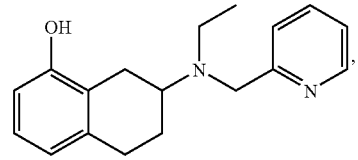

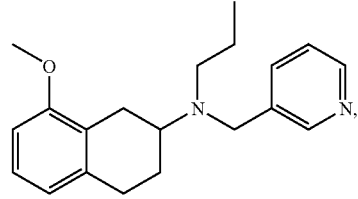

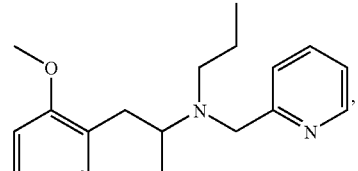

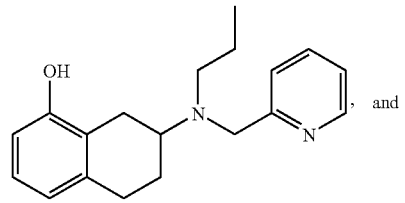

-continued

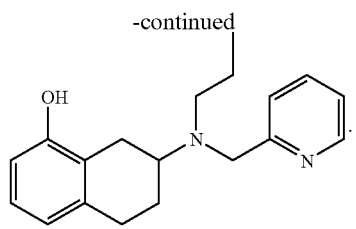

7. A pharmaceutical composition comprising a compound having formula 1

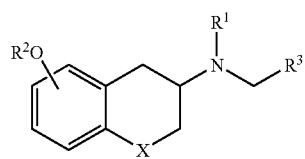

Formula 1 wherein:
R$^1$=H, methyl, ethyl, propyl, or cyclobutyl;
R$^2$=methyl or H;
R$^3$=pyridinyl;
X=C.

8. The pharmaceutical composition of claim 7, wherein R$^1$ is ethyl or propyl.

9. The pharmaceutical composition of claim 8, wherein R$^2$ is H or methyl.

10. The pharmaceutical composition of claim 8, wherein R$^3$ is selected from the group consisting of

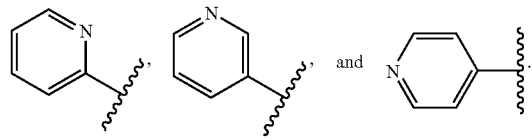

11. The pharmaceutical composition of claim 7, wherein X is C.

12. The pharmaceutical composition of claim 7, wherein said compound is selected from the group consisting of:

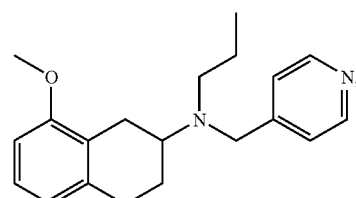

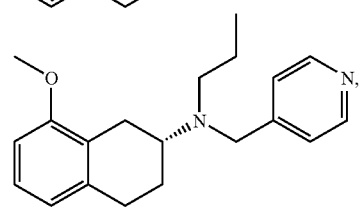

-continued

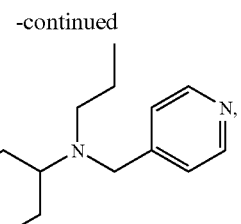

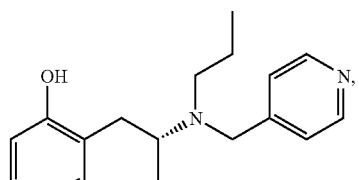

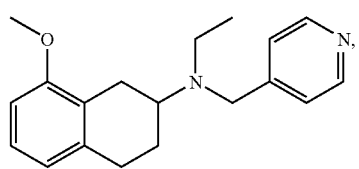

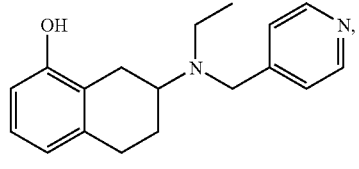

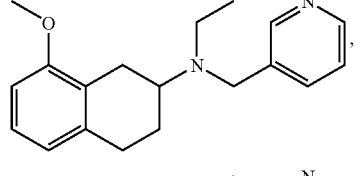

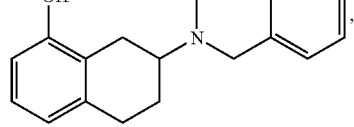

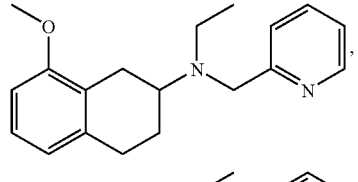

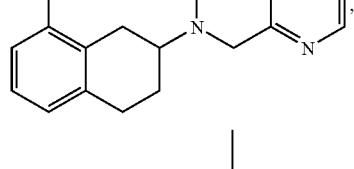

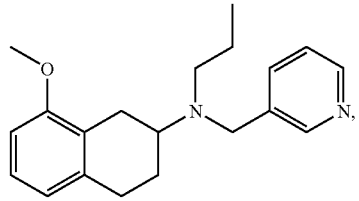

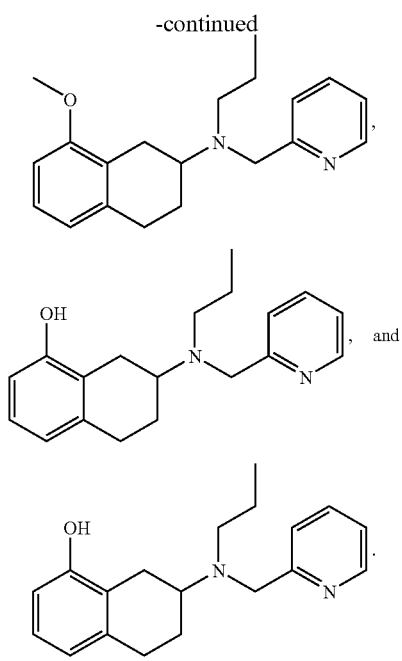

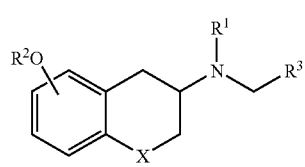

13. A method of treating an alpha 2B receptor mediated disease or condition, comprising administering to a mammal in need thereof, a therapeutically effective amount of a compound having formula 1

Formula 1 wherein:
R$^1$=H, methyl, ethyl, propyl, or cyclobutyl;
R$^2$=methyl or H;
R$^3$=pyridinyl;
X=C; and a pharmaceutically acceptable carrier, wherein said disease or condition is selected from the group consisting of chronic pain, visceral pain, neuropathic pain, corneal pain, glaucoma, elevated intraocular pressure, ischemic neuropathies, neurodegenerative diseases, diarrhea, nasal congestion, muscle spasticity, diuresis, withdrawal syndromes, neurodegenerative diseases, optic neuropathy, spinal ischemia, stroke, memory and cognition deficits, attention deficit disorder, psychoses, manic disorders, anxiety, depression, hypertension, congestive heart failure, cardiac ischemia, arthritis, spondylitis, gouty arthritis, osteoarthritis, juvenile arthritis, autoimmune diseases, lupus erythematosus, chronic gastrointestinal inflammations, Crohn's disease, gastritis, irritable bowel syndrome (IBS), functional dyspepsia, and ulcerative colitis.

14. The method of claim 13, wherein R$^1$ is ethyl or propyl.

15. The method of claim 13, wherein R$^2$ is H or methyl.

16. The method of claim 13, wherein R$^3$ is ethyl.

17. The method of claim 13, wherein R$^3$ is selected from the group consisting of

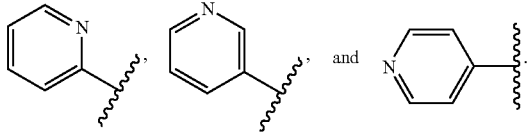

18. The method of claim 13, wherein said compound is selected from the group consisting of

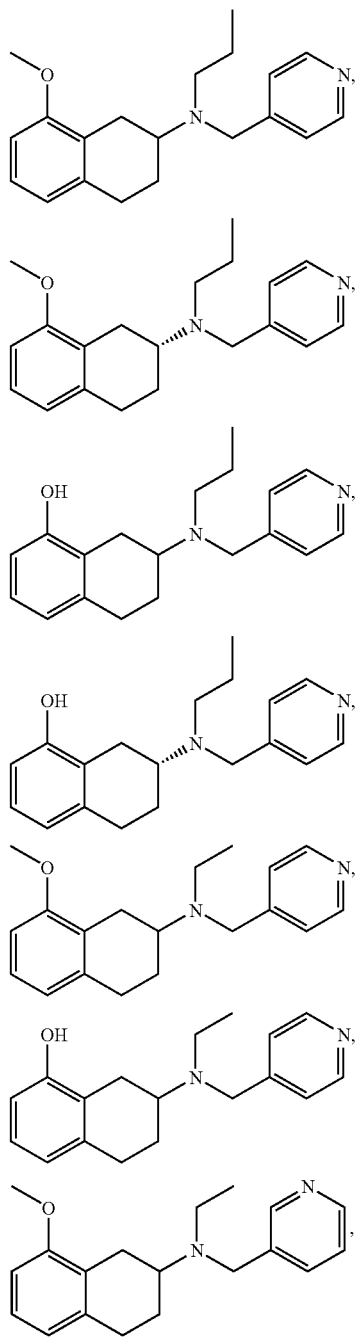

-continued
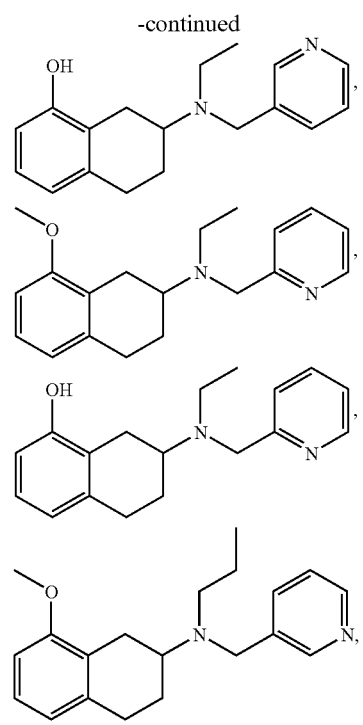
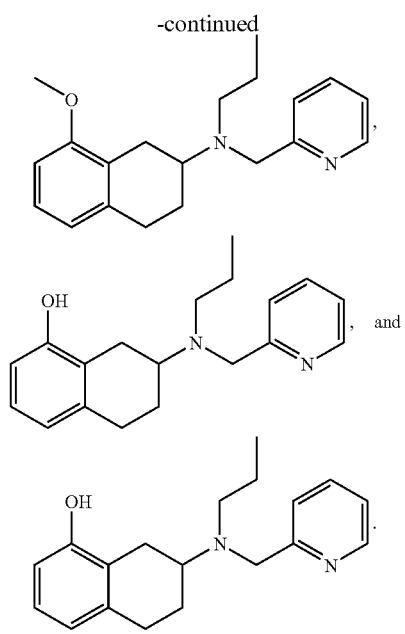
19. The method of claim 13, wherein X is C.
* * * * *